(12) United States Patent
Schade

(10) Patent No.: US 10,130,749 B2
(45) Date of Patent: Nov. 20, 2018

(54) MEDICAL DEVICE FOR EXTRACORPOREAL BLOOD TREATMENT COMPRISING PLURAL SENSOR UNITS

(71) Applicant: B. Braun Avitum AG, Melsungen (DE)

(72) Inventor: Andreas Schade, Rotenburg (DE)

(73) Assignee: B. BRAUN AVITUM AG, Melsungen (DE)

( * ) Notice: Subject to any disclaimer, the term of this patent is extended or adjusted under 35 U.S.C. 154(b) by 600 days.

(21) Appl. No.: 13/900,685

(22) Filed: May 23, 2013

(65) Prior Publication Data

US 2013/0317408 A1 Nov. 28, 2013

(30) Foreign Application Priority Data

May 23, 2012 (DE) .......................... 10 2012 104 461

(51) Int. Cl.
*A61M 1/36* (2006.01)
*A61B 5/00* (2006.01)
*A61B 5/1455* (2006.01)

(52) U.S. Cl.
CPC .......... *A61M 1/3624* (2013.01); *A61B 5/6866* (2013.01); *A61M 1/367* (2013.01); *A61B 5/14557* (2013.01); *A61M 2209/088* (2013.01)

(58) Field of Classification Search
CPC ............. A61B 5/14557; A61B 5/6866; A61M 1/3624; A61M 2209/088;
(Continued)

(56) References Cited

U.S. PATENT DOCUMENTS 4,136,818 A 1/1979 Larrabee
4,231,366 A * 11/1980 Schael .................... A61M 1/30
128/DIG. 13
(Continued)

FOREIGN PATENT DOCUMENTS

CA 2976872 A1 4/2010
DE 285637 A5 12/1990
(Continued)

OTHER PUBLICATIONS

European Search Report for EP 13 16 7902 dated Aug. 26, 2013.
(Continued)

*Primary Examiner* — Tatyana Zalukaeva
*Assistant Examiner* — Kai Weng
(74) *Attorney, Agent, or Firm* — RatnerPrestia

(57) ABSTRACT

The invention relates to a medical device for extracorporeal blood treatment comprising an extracorporeal blood circulation having at least one tube and at least two sensor units measuring on the tube with different operating principles, wherein portions of the tube are adapted to be coupled to the at least two sensor units for measurement. According to the invention, each sensor unit consists of a sensor-specific component and a sensor-neutral component, wherein the sensor-neutral components of the sensor units are formed to be identical whereas the sensor-specific components are different in response to the operating principle and comprise a respective specific sensor system. Furthermore, for each sensor unit a sensor-neutral component is mounted on a sensor-specific component, wherein when being introduced and fixed in a sensor-neutral component a portion of the tube is adapted to be coupled to the sensor system of the sensor-specific component located there beneath so that the sensor system can carry out a measurement at the tube.

12 Claims, 4 Drawing Sheets

(58) Field of Classification Search
CPC ........... A61M 2209/082; A61M 5/1684; G01F 23/292; G01F 25/0061
See application file for complete search history.

(56) References Cited

U.S. PATENT DOCUMENTS

| | | | |
|---|---|---|---|
| 4,722,224 | A | 2/1988 | Scheller et al. |
| 4,764,166 | A | 8/1988 | Spani |
| 5,123,275 | A | 6/1992 | Daoud et al. |
| 5,135,485 | A * | 8/1992 | Cohen ................. A61M 5/1684 324/606 |
| 5,335,551 | A * | 8/1994 | Ohnishi ............... A61M 1/3639 338/4 |
| 5,394,732 | A | 3/1995 | Johnson et al. |
| 5,595,182 | A | 1/1997 | Krivitski |
| 5,672,887 | A | 9/1997 | Shaw et al. |
| 5,685,989 | A | 11/1997 | Krivitski et al. |
| 6,144,444 | A | 11/2000 | Haworth et al. |
| 6,268,910 | B1 | 7/2001 | Samsoondar et al. |
| 6,623,443 | B1 | 9/2003 | Polaschegg |
| 7,243,541 | B1 | 7/2007 | Bey et al. |
| 7,381,195 | B2 | 6/2008 | Mori et al. |
| 2004/0064049 | A1 | 4/2004 | Doten |
| 2005/0070845 | A1 | 3/2005 | Faries et al. |
| 2006/0079786 | A1 | 4/2006 | Stofer et al. |
| 2009/0293588 | A1 | 12/2009 | Riley et al. |
| 2011/0009800 | A1 | 1/2011 | Dam et al. |
| 2011/0130741 | A1 * | 6/2011 | Miles .................. G01N 29/032 604/500 |
| 2012/0277673 | A1 | 11/2012 | Levin et al. |

FOREIGN PATENT DOCUMENTS

| | | |
|---|---|---|
| DE | 69219132 T2 | 7/1997 |
| DE | 698 35 142 | 9/1998 |
| DE | 199 01 078 | 2/2000 |
| DE | 10243069 B4 | 7/2006 |
| DE | 102010047248 A1 | 4/2012 |
| DE | 102011084171 A1 | 5/2012 |
| EP | 0 720 013 | 7/1996 |
| EP | 0720013 A2 | 7/1996 |
| WO | 9837802 A1 | 9/1998 |
| WO | 2008118600 A1 | 10/2008 |
| WO | WO 2010/136962 | 12/2010 |
| WO | 2012031206 A2 | 3/2012 |
| WO | WO 2012/044812 | 4/2012 |

OTHER PUBLICATIONS

German Search Report for DE 10 2012 104 461.9 dated Dec. 10, 2012.
Opposition Proceedings for EP Application No. 2666492, dated Jul. 14, 2016 with unchecked machine translation, 62 pages.
Nikkiso—"Operating Instructions DBB-07, Software Version 3.0," Feb. 2012, pp. 1-19, 1-36, 2-6.
Nikkiso—"Online-therapy a: the focus—Dialysis System DBB-07," Jun. 2016, 4 pages.
Grounds of Appeal for EP Application No. 2666492, dated Jul. 3, 2018 with unchecked machine translation, 97 pages.

* cited by examiner

MEDICAL DEVICE FOR EXTRACORPOREAL BLOOD TREATMENT COMPRISING PLURAL SENSOR UNITS

CROSS REFERENCE TO RELATED APPLICATIONS

This application claims priority to German Patent Application No. DE 10 2012 104 461.9 filed May 23, 2012, the contents of such application being incorporated by reference herein.

FIELD OF THE INVENTION

The invention relates to a medical device for extracorporeal blood treatment comprising an extracorporeal blood circulation having at least one tube and at least two sensor units of different operating principles to which sensor units portions of the tube are adapted to be coupled for measurement during the therapy.

BACKGROUND INFORMATION

In medical devices for extracorporeal blood treatment an extracorporeal blood circulation is built up via tubes and chambers, wherein usually a single-use article in the form of a tube is employed for this purpose which the operator fastens to the device for therapy. To enable the operator to perform the fastening in the provided way, appropriate holding means are arranged on the device. Furthermore during treatment of patients various parameters are detected with the aid of sensors and measuring systems, respectively. Since direct contact of the sensors with the blood of the patient usually is not desired and not necessary, respectively, the measurements are frequently performed on a tube portion of the single-use article. It may be necessary, for achieving the desired measuring results, to attach the single-use article employed to a desired position at the device and the sensor.

Since the single-use article is attached to the device by the operator of the device, it is also up to the operator to place the same in the provided and technically required way. However, the operator cannot necessarily be expected to know the functioning of the respective measuring system and to be able to appropriately take the latter into account. Therefore it is recommended to standardize the steps to be taken by the operator for inserting the single-use article for systems measuring on the tube.

However, in the known devices the operator is frequently confronted with different steps not directly reproducible to him/her at different measuring systems. Moreover, deviations from the provided proceeding can have negative effects on the functioning of the measuring systems.

SUMMARY OF THE INVENTION

Therefore, it is an object of at least one aspect of the invention to provide a medical device for extracorporeal blood treatment comprising at least two sensor units measuring on a tube of different operating principles to which sensor units a tube portion of the extracorporeal blood circulation has to be coupled for measurement during the therapy, wherein the steps required for attaching the tube are intended to be standardized.

The medical device for extracorporeal blood treatment according to aspects of the invention comprises an extracorporeal blood circulation including at least one tube and at least two sensor units measuring on the tube with different operating or measuring principles, wherein portions of the tube can be coupled for measurement to the at least two sensor units. Each sensor unit consists of a sensor-specific component and a sensor-neutral component, the sensor-neutral components of the sensor units being formed to be identical, whereas the sensor-specific components are different dependent on the respective operating or measuring principle and comprise a specific sensor system. Furthermore, for each sensor unit a sensor-neutral component is mounted on a sensor-specific component, wherein a portion of the tube when being introduced and fixed in a sensor-neutral component is adapted to be coupled to the sensor system of the sensor-specific component located there beneath so that by the sensor system a measurement can be performed at the tube.

The sensor-neutral components of each sensor unit are thus identical independently of the operating principle of the associated sensor system and only the sensor-specific components are different from each other. From outside each sensor unit is then presented to be equal to the operator as the sensor-neutral components are mounted above the sensor-specific components. The sensor-neutral components predetermine the proceeding for inserting and fixing a tube portion within the sensor unit which proceeding is equal for each sensor unit. The structure of the sensor unit ensures, however, that the tube portion is simultaneously coupled to a sensor system arranged below the sensor-neutral component so that a measurement can be carried out. Thus, upon inserting a tube the operator need not know the functioning of the respective sensor system, but he/she can insert the tube in every sensor unit in the same way and the structure of the sensor unit automatically results in coupling the tube to the respective sensor system.

In an embodiment of the invention each of the sensor-neutral and sensor-specific components have differently formed base members and the base members of the sensor-neutral components enclose the respective base members of the sensor-specific components located there beneath. In this way, when such sensor unit is mounted on the housing of a medical device, only the sensor-neutral component is visible from outside.

Preferably the base members of the sensor-neutral components have a recess and a portion of the tube can be introduced into the sensor-neutral components so that the portion of the tube is adapted to be coupled to the sensor system of a sensor-specific component through the recess. In this way it is ensured with components mounted on top of each other that a tube portion inserted in the upper component is adapted to be coupled to the sensor system located there beneath for measurement.

In an embodiment of the invention each sensor-specific component includes a tube channel into which the portion of a tube can be inserted. Thus the tube can be aligned and fixed with respect to the sensor system. The tube channels of at least two sensor-specific components can also be formed to be different. For example, they can include different bores for coupling sensors to the tube or other means required for measurement.

In order to connect the tube channel of a sensor-specific component to the associated sensor-neutral component so that a tube inserted in the sensor-neutral component is located within the tube channel as prescribed and is coupled to the sensor system, each sensor-neutral component may include two channel-type tube holders with the recess provided there between. These tube holders are preferably adjacent to the two ends of the tube channel such that a continuous tube channel is resulting. For the operator the combination of two tube holders and the tube channel of the sensor-specific component located there between thus presents itself as continuous tube channel into which the tube has to be inserted.

For fixing an inserted tube within the sensor unit each sensor-neutral component may have a cover by which the portion of a tube is adapted to be pressed against the sensor system of the associated sensor-specific component in a closed and locked position. When such cover is arranged, it is thus adjacent to the tube and causes a pressure onto the tube in the direction of the sensor system. In this way the tube can be fixed within a tube channel. For being capable of specifically applying such pressure the cover may have at least one pressure element protruding from the cover by which pressure can be applied to the portion of a tube.

However, the tube can also be fixed to the sensor unit in other ways. For this, e.g. brackets, clamping elements, elastic tensioning means etc. are taken into account. Also the pressure applied to the tube within a tube within can be generated, apart from a pressure element, by supplementary or alternative means.

If, however, the described cover is provided, it is preferably pivoted to the respective base member of the sensor-neutral component and in the closed position is lockable to the base member. For such locking at least one detent element can be provided at each of the cover and the base member. When the cover is pressed against the base member of the sensor-neutral component in the closed position, these detent elements are engaged so as to hold the cover in this position. However, they are configured to enable the engagement to be manually disengaged again by pulling the cover and/or pressing on the detent elements.

The closure mechanism of the sensor unit is preferably formed exclusively at the sensor-neutral component. This is also applicable to possibly required seals of the sensor unit to the outside.

The invention in this way enables systems measuring on the tube of different operating principles to be configured in a standardized manner for the operator. This is especially advantageous for the use of optical and/or thermal sensor systems, ultrasonic sensors, tactile sensors and/or pressure sensors. Measuring errors due to operation are excluded or at least minimized in this way and the operator has to memorize only one course of action, because the sensor units of the medical device for extracorporeal blood treatment have a uniform appearance and clear semantics. The steps to be taken by the operator are independent of the measuring principle of the respective sensor unit.

Furthermore, the use of identical parts results in a reduction of costs, for the identical sensor-neutral components can be manufactured inexpensively and can be used for plural sensor units. This is especially advantageous in view of a solution in which plural sensor units of a medical device permit the same insertion of a tube in each case, but for this each sensor unit has to exhibit a specific component configuration so as to simultaneously enable the tube to be coupled to the respective sensor system. Such solution would allow fewer identical parts to be employed.

BRIEF DESCRIPTION OF THE DRAWINGS

The invention is best understood from the following detailed description when read in connection with the accompanying drawings. Included in the drawings are the following figures.

DETAILED DESCRIPTION OF THE PREFERRED EMBODIMENTS

Figure 1:
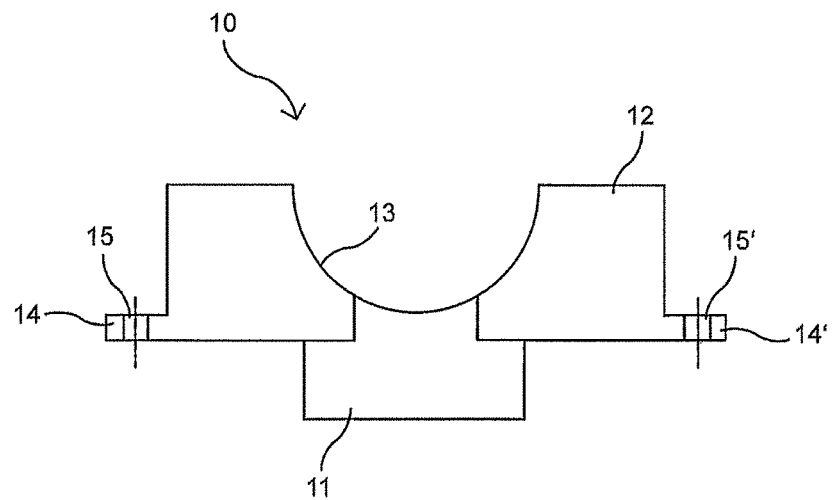
FIG. 1 shows a schematic side view of an embodiment of a sensor-specific component.

FIG. 1 shows a schematic side view of an embodiment of a sensor-specific component 10. The component is substantially constituted by a base member 12 in the center of which a tube channel 13 is formed. The latter can also be referred to as tube acceptance as it serves for accepting and aligning the tube within the sensor unit. It can have an approximately semicircular cross-section as in the shown embodiment. The cross-section may also be different, however.

Below said tube channel 13 at or in the base member 12 the sensor system 11 of the sensor-specific component 10 is arranged which can also be referred to as measuring system. Said sensor system 11 differs from the sensor systems of other sensor-specific components and is dependent on the operating principle of the respective sensor unit. However, the sensor system 11 need not be arranged in the center directly below the tube channel 13, but it can also be coupled from the side to a tube introduced into the tube channel 13, for example. The shapes of the tube channels of the respective sensor-specific components may be different. Moreover, the shapes of the base members 12 of the different sensor-specific components 10 can be different as long as they are configured in such way that a standard sensor-neutral component can be mounted on them.

At the sides of the base member 12 mounting tabs 14 and 14' are formed by which the sensor-specific component 10 can be attached to the housing of a medical device for extracorporeal blood treatment (not shown). For instance, mounting bores 15 and 15' can be provided within the mounting tabs 14, 14' for this purpose. When mounted at a housing, the sensor system 11 is preferably arranged inside the housing so that a recess must be provided in the housing. The base member 12, on the other hand, protrudes from the housing.

Figure 2:
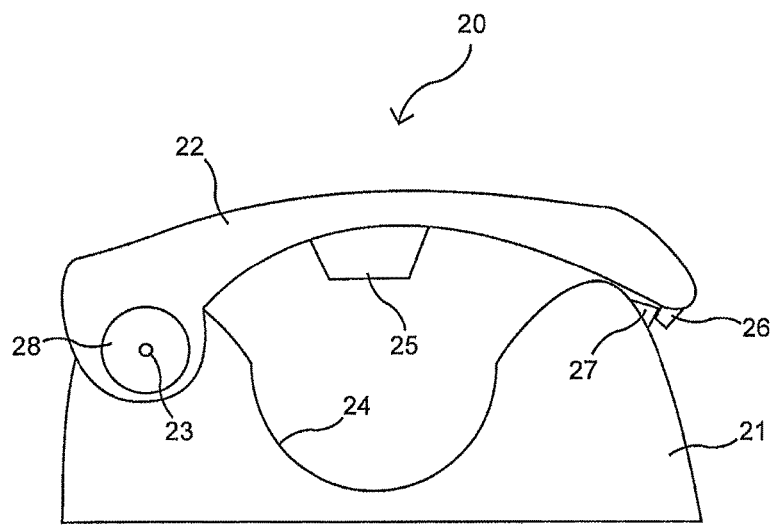
FIG. 2 shows a schematic side view of an embodiment of a sensor-neutral component.
Figure 3:
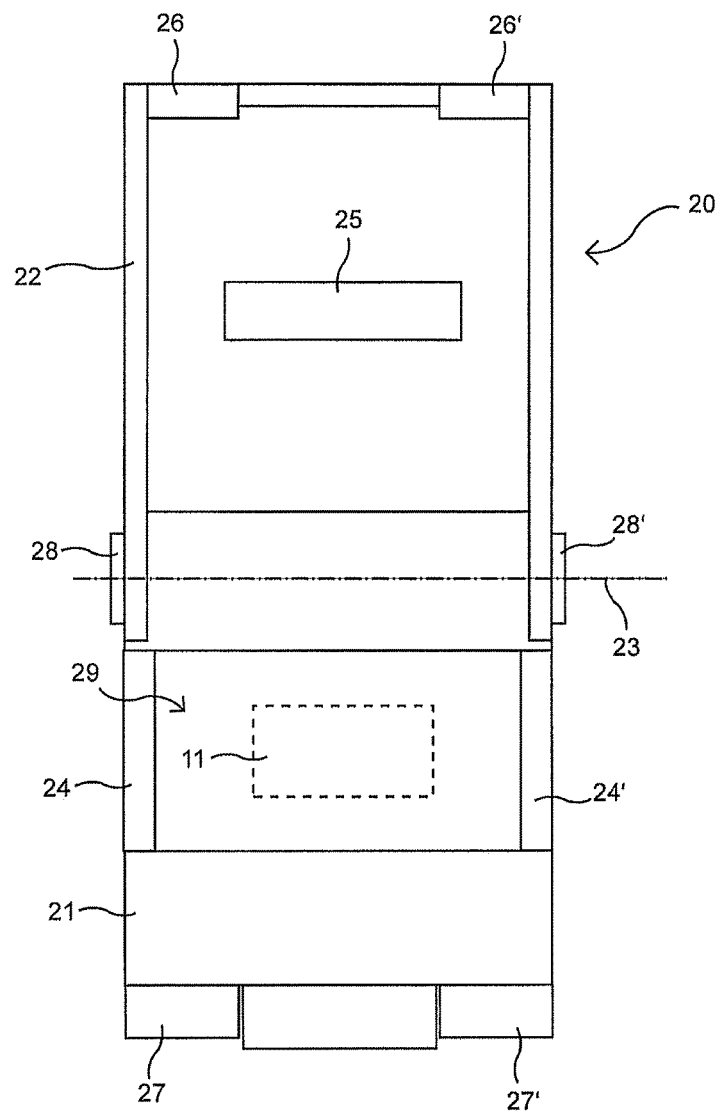
FIG. 3 shows a schematic top view of a sensor-neutral component having an opened cover.

FIG. 2 illustrates a schematic side view of an embodiment of a sensor-neutral component 20. Said component 20 equally consists of a base member 21 in which at least one channel-type tube holder is formed. This is not a continuous channel, however, but two narrow channels 24 and 24' spaced apart from each other by a recess 29. This is especially visible from the top view of FIG. 3. FIG. 3 also shows a sensor system 11 of a sensor-specific component 10 in broken lines within the recess 29 to illustrate the way in which the sensor system 11 can be contacted through the sensor-neutral component 20 by a tube inserted in the sensor-neutral component 20.

The sensor-neutral component 20 further includes a cover 22 pivoted to the base member 21 of the component 20. The cover 22 can be pivoted to the base member 21 via two lateral bolts 28 and 28', for example. The cover 22 is supported via a pivot axis 23 such that the cover 22 can be opened so as to be capable of introducing the portion of a tube into the tube holders 24, 24'. When the tube has been introduced the cover can be closed by pivoting and can be locked to the base member 21 by detent elements. For this, e.g. two detent lugs 27 and 27' are attached to the base member 21 as they can also be inferred from the top view of FIG. 3. At the cover 22 there are equally provided two detent lugs 26 and 26' that engage below the detent lugs 27, 27' of the base member 21 when the cover 22 is pressed down.

Figure 4:
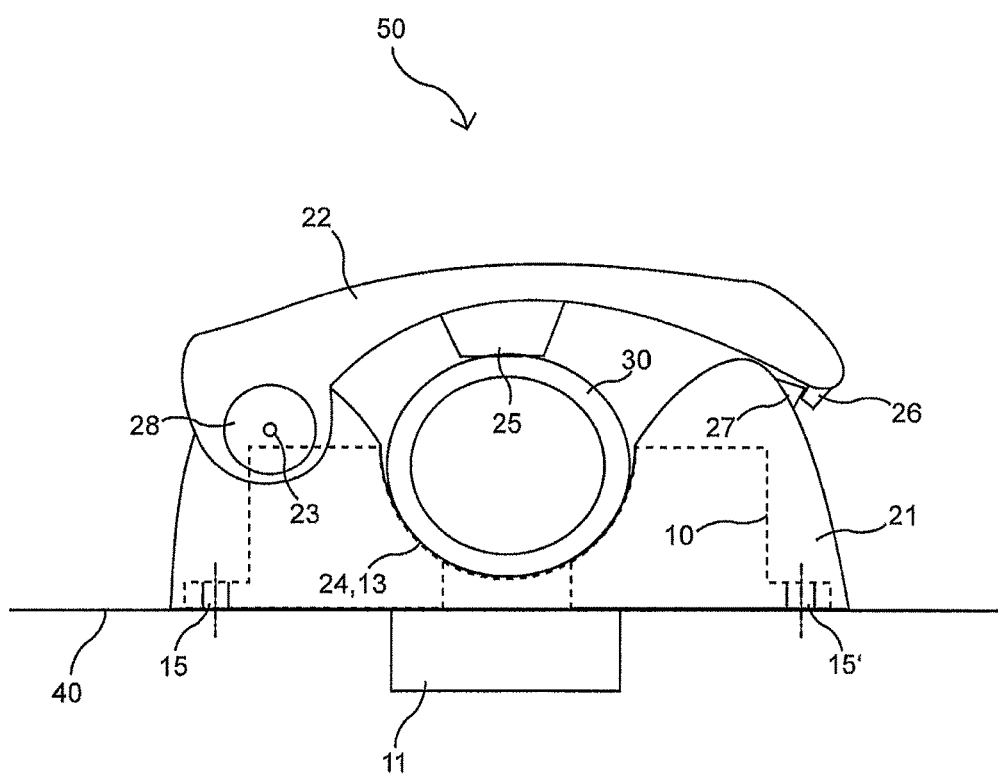
FIG. 4 is a schematic side view of a mounted sensor unit with introduced tube.

A pressure element 25 protruding downwardly in the closed position of the cover can be formed at the inside of the cover 22. Hereby an introduced tube can be pressed in the direction of the sensor system 11 of a sensor-specific component 10, for the sensor-neutral component 20 preferably can be completely slipped on the sensor-specific component 10 and can be equally mounted on the housing of a medical device for extracorporeal blood treatment. This is shown in FIG. 4, wherein the sensor-specific component 10 mounted below the sensor-neutral component 20 is shown in broken lines.

Both components 10 and 20 are mounted on a housing 40 and jointly form a sensor unit 50. For such assembly also mounting bores or other fasteners can be provided at the sensor-neutral component 20. The sensor-neutral component can be fastened to the housing or the sensor-neutral component is fixed to the sensor-specific component which in turn is fastened to the housing.

According to the invention, at least two of these sensor units 50 are arranged at a medical device for extracorporeal blood treatment, the external sensor-neutral components 20 being always identical, whereas the sensor-specific components 10 located there beneath are different in response to the operating principle of the associated sensor system 11. However, for the operator each sensor unit 50 appears to be equal so that for inserting and fixing a tube 30 within a sensor unit 50 no knowledge of the respective sensor system 11 is necessary. Irrespective of the sensor system 11, the operator can insert and fix the tube 30 in each sensor unit 50 in the same way, as this is predetermined by the external sensor-neutral component 20, and the coupling to the sensor-specific component 10 located there beneath is realized by appropriate engagement of the two components.

Figure 5:
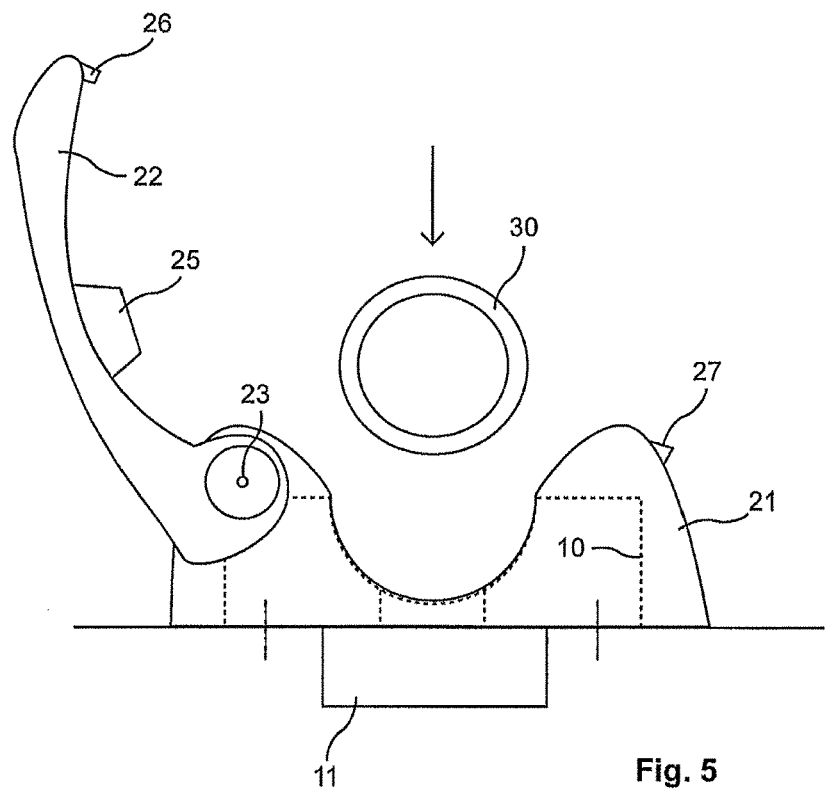
FIG. 5 shows a sensor unit upon inserting a tube.
Figure 6:
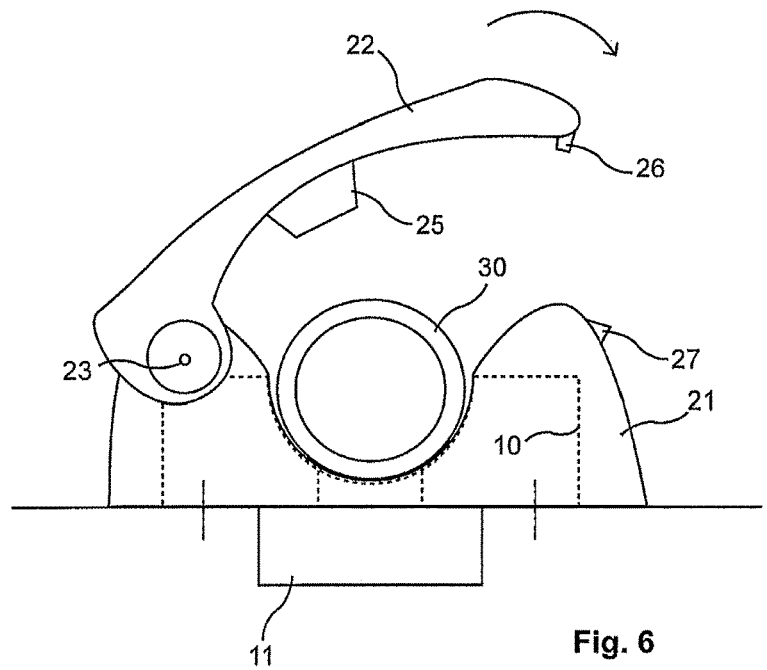
FIG. 6 shows a sensor unit upon closing the cover.

For inserting the tube the operator opens the cover 22 by pivoting the same about the pivot 23 and inserts the tube 30 into the sensor unit 50 as is illustrated in FIG. 5 by an arrow pointing downwards. The tube holders 24 and 24' of the sensor-neutral component 20 are adjacent to both side of the tube channel 13 of the sensor-specific component 10 so that from above the operator can see a continuous tube channel into which the tube 30 can be inserted. After that the cover 22 is pivoted to the closed position as shown in FIG. 6 by a bent arrow. As soon as the pressure element 25 contacts the inserted tube 30, it presses the latter against the sensor system 11 of the sensor-specific component 10 so that a safe contact is established between the tube 30 and the sensor system 11. Furthermore the cover 22 engages in the base member 21 via the detent lugs 26, 26', 27 and 27'. For removing the tube 30 from the sensor unit 50 again after a therapy the engagement is configured in such way that the cover 22 can be manually disengaged therefrom again.

The invention claimed is:

1. A medical device for extracorporeal blood treatment comprising:
    a housing; and
    an extracorporeal blood circulation having:
        a tube, and
        at least two sensor units mounted to the housing of the medical device with different operating principles measuring directly on the tube and not on a chamber, wherein:
            the at least two sensor units are coupled to portions of the tube for measurement, and
            each sensor unit comprises a respective sensor-specific component and a respective sensor-neutral component, wherein:
                each of the respective sensor-specific components includes a base member mounted to the housing of the medical device, and a respective specific sensor system formed to be different dependent on a respective operating principle, and
                each of the respective sensor-neutral components includes a housing fully enclosing one of the respective sensor-specific components, wherein each of the sensor-neutral components are identical;
                each of the respective sensor-neutral components is mounted on and encloses the respective sensor-specific component for each sensor unit such that the respective sensor-specific component is not visible when the sensor unit is mounted on the housing of the medical device, and wherein the respective specific sensor system of the respective sensor-specific component is located beneath a portion of the tube when the tube is fixed within the sensor-neutral component mounted on the respective sensor-specific component, such that the respective specific sensor system carries out a respective measurement at the tube; and wherein
                each respective sensor-neutral component has a cover, wherein in a closed and locked position the portion of the tube is pressed against the sensor system of the associated respective sensor-specific component and in an open position the portion of the tube is not pressed against the sensor system.

2. The medical device according to claim 1, wherein the respective sensor-neutral and respective sensor-specific components each have differently formed base members and the base members of the respective sensor-neutral components enclose the base members of the respective sensor-specific components located there beneath.

3. The medical device according to claim 2, wherein the base members of the respective sensor-neutral components include a recess configured to receive a portion of the tube at the respective sensor-neutral components so that the portion of the tube is coupled to the respective specific sensor system of each respective sensor-specific component through the recess.

4. The medical device according to claim 3, wherein each respective sensor-specific component includes a tube channel into which the portion of the tube can be inserted.

5. The medical device according to claim 4, wherein the tube channels of at least two respective sensor-specific components are formed differently.

6. The medical device according to claim 4, wherein each respective sensor-neutral component has two channel-type tube holders with the recess located there between and that the tube holders are located at the two ends of the tube channel of the respective sensor-specific component so that a continuous tube channel is resulting.

7. The medical device according to claim 1, wherein the cover includes at least one pressure element protruding from the cover by which pressure is applicable to the portion of the tube.

8. The medical device according to claim 1, wherein the cover is pivoted to the respective base member of the respective sensor-neutral component and is adapted to be locked in a closed position at the base member.

9. The medical device according to claim 8, wherein at least one detent element is provided for locking at the cover at the base member.

10. The medical device according to claim 5, wherein each respective sensor-neutral component has two channel-type tube holders with the recess located there between and that the tube holders are located at the two ends of the tube channel of the respective sensor-specific component so that a continuous tube channel is resulting.

11. The medical device according to claim 7, wherein the cover is pivoted to the respective base member of the respective sensor-neutral component and is adapted to be locked in a closed position at the base member.

12. A medical device for extracorporeal blood treatment comprising:
    a housing; and
    an extracorporeal blood circulation having:
        a tube, and
        at least two sensor units mounted to the housing of the medical device with different operating principles measuring directly on the tube and not on a chamber, wherein:
            the at least two sensor units are coupled to portions of the tube for measurement, and
            each sensor unit comprises a respective sensor-specific component and a respective sensor-neutral component, wherein:
                each of the respective sensor-specific components includes a base member mounted to the housing of the medical device, and a respective specific sensor system formed to be different dependent on a respective operating principle, and
                each of the respective sensor-neutral components includes a housing fully enclosing one of the respective sensor-specific components, wherein each of the sensor-neutral components are identical; and wherein
                each of the respective sensor-neutral components is mounted on and encloses the respective sensor-specific component for each sensor unit such that the respective sensor-specific component is not visible when the sensor unit is mounted on the housing of the medical device, and wherein the respective specific sensor system of the respective sensor-specific component is located beneath a portion of the tube when the tube is fixed within the sensor-neutral component mounted on the respective sensor-specific component, such that the respective specific sensor system carries out a respective measurement at the tube.

* * * * *